United States Patent
Dadd et al.

(10) Patent No.: US 7,555,352 B2
(45) Date of Patent: Jun. 30, 2009

(54) IMPLANTABLE CARRIER MEMBER HAVING A NON-COMMUNICATIVE LUMEN

(75) Inventors: Fysh Dadd, Lane Cove (AU); Peter Gibson, South Coogee (AU); Claudiu Treaba, Wollstonecraft (AU)

(73) Assignee: Cochlear Limited, Lane Cove (AU)

( * ) Notice: Subject to any disclaimer, the term of this patent is extended or adjusted under 35 U.S.C. 154(b) by 544 days.

(21) Appl. No.: 11/268,592

(22) Filed: Nov. 8, 2005

(65) Prior Publication Data

US 2007/0106360 A1 May 10, 2007

(51) Int. Cl.
*A61N 1/05* (2006.01)
(52) U.S. Cl. ...................................... 607/137
(58) Field of Classification Search .................. 607/115, 607/136, 137
See application file for complete search history.

(56) References Cited

U.S. PATENT DOCUMENTS

| 5,653,742 A * | 8/1997 | Parker et al. ................. 607/137 |
| 6,321,125 B1 * | 11/2001 | Kuzma ....................... 607/137 |
| 6,968,238 B1 * | 11/2005 | Kuzma ....................... 607/137 |
| 7,319,906 B2 * | 1/2008 | Kuzma et al. ............... 607/137 |

* cited by examiner

*Primary Examiner*—Carl H Layno
*Assistant Examiner*—Brian T Gedeon
(74) *Attorney, Agent, or Firm*—Connolly Bove Lodge & Hutz LLP

(57) ABSTRACT

A non-communicative lumen for electrode assemblies of medical implants, in particular prosthetic hearing implants, is provided by the present invention. The non-communicative lumen prevents the lumen within the cochlea from being able to transport fluids, cells, bacteria, tissue, etc., with the lumen outside the cochlea, and vise versa through the incision or cochleostomy. The lumen may have a cavity or slit that receives a stylet during insertion of the electrode assembly.

65 Claims, 10 Drawing Sheets

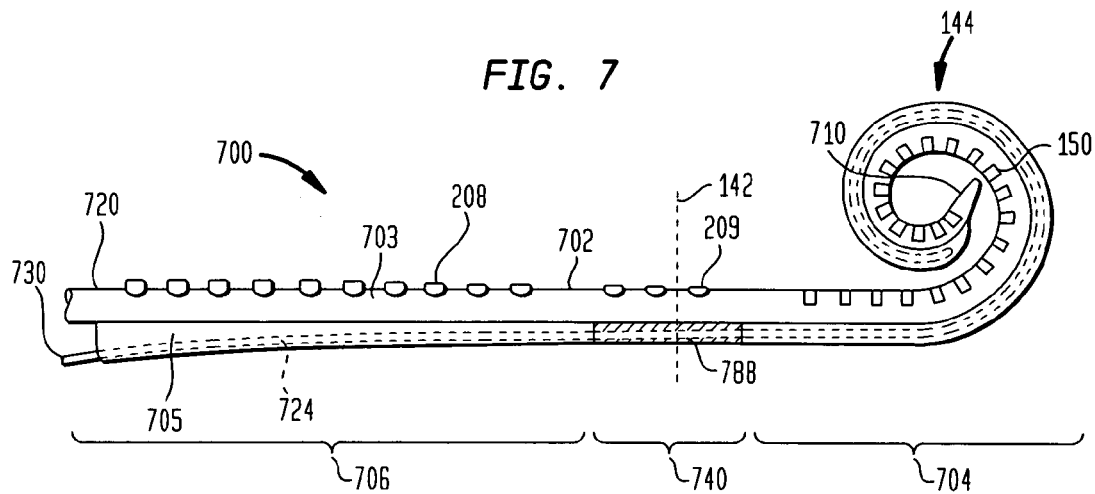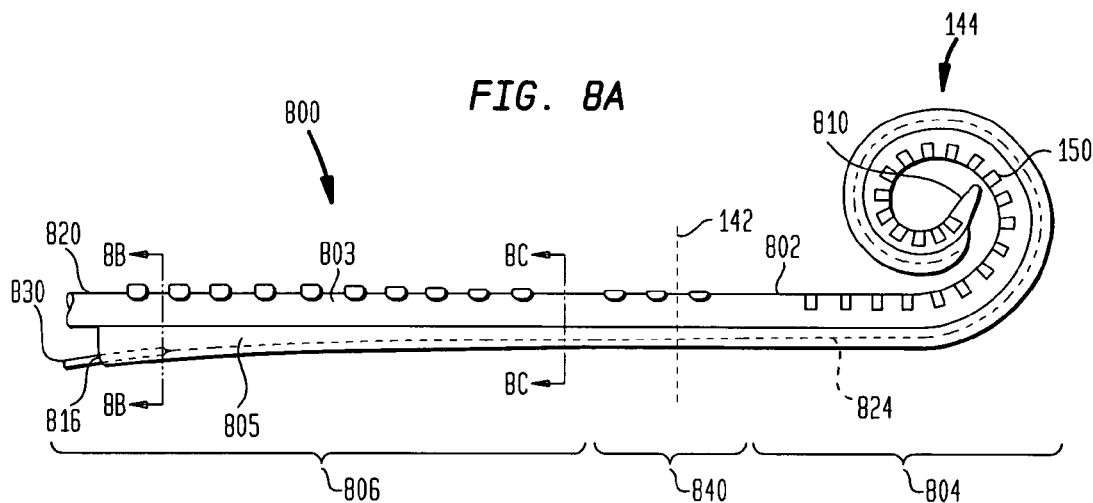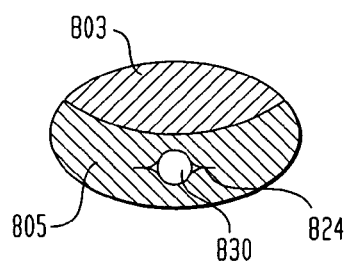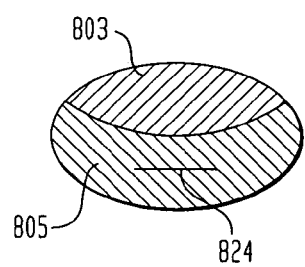

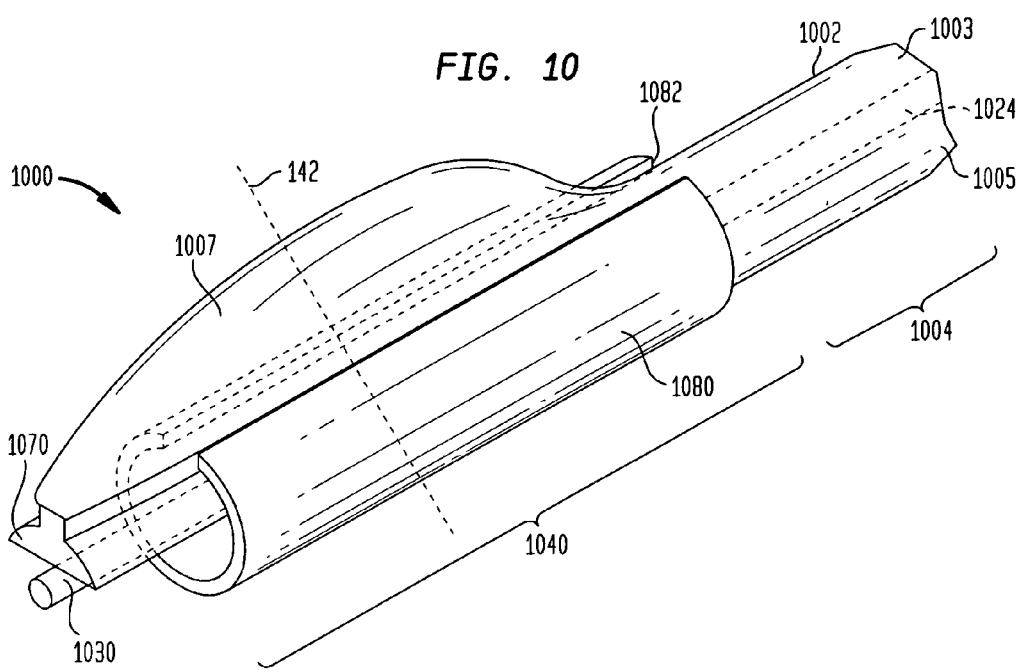
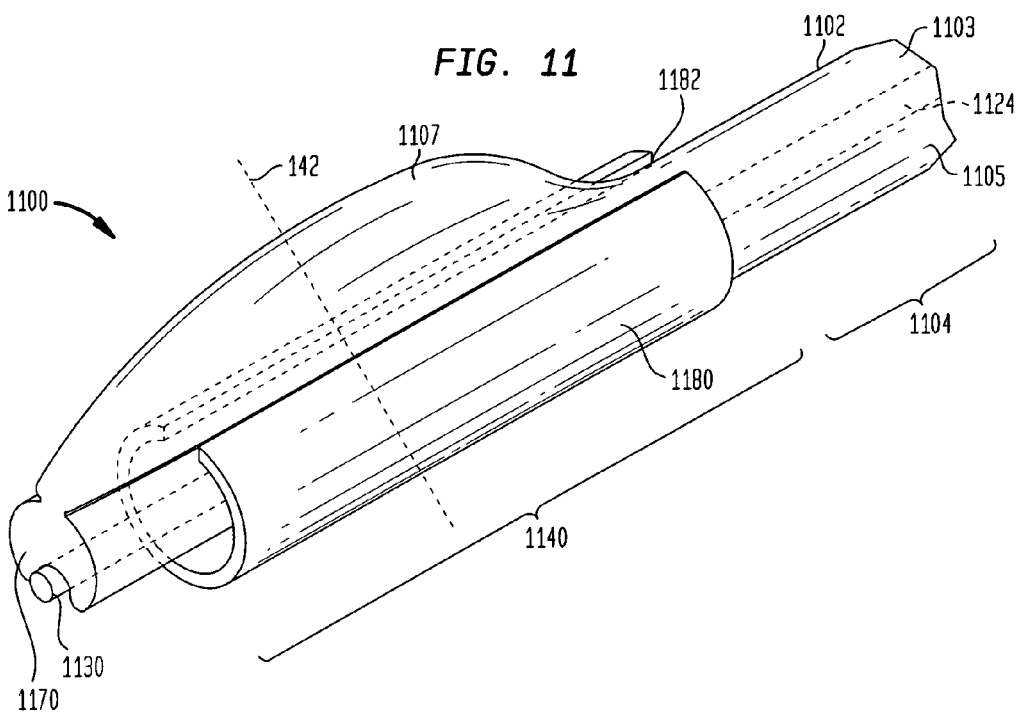

IMPLANTABLE CARRIER MEMBER HAVING A NON-COMMUNICATIVE LUMEN

BACKGROUND

1. Field of the Invention

The present invention relates generally to electrode assemblies and, more particularly, to a non-communicative lumen for an electrode assembly.

2. Related Art

There are a variety of medical implants which deliver electrical stimulation to a patient or recipient ("recipient" herein) for a variety of therapeutic benefits. For example, the hair cells of the cochlea of a normal healthy ear convert acoustic signals into nerve impulses. People who are profoundly deaf due to the absence or destruction of cochlea hair cells are unable to derive suitable benefit from conventional hearing aid systems. Prosthetic hearing implant systems have been developed to provide such persons with the ability to perceive sound. Prosthetic hearing implant systems bypass the hair cells in the cochlea to directly deliver electrical stimulation to auditory nerve fibers, thereby allowing the brain to perceive a hearing sensation resembling the natural hearing sensation.

The electrodes implemented in stimulating medical implants vary according to the device and tissue which is to be stimulated. For example, the cochlea is tonotopically mapped and partitioned into regions, with each region being responsive to stimulus signals in a particular frequency range. To accommodate this property of the cochlea, prosthetic hearing implant systems typically include an array of electrodes each constructed and arranged to deliver an appropriate stimulating signal to a particular region of the cochlea.

To achieve an optimal electrode position close to the inside wall of the cochlea, the electrode assembly should assume this desired position upon or immediately following implantation into the cochlea. It is also desirable that the electrode assembly be shaped such that the insertion process causes minimal trauma to the sensitive structures of the cochlea. Usually the electrode assembly is held in a straight configuration at least during the initial stages of the insertion procedure, conforming to the natural shape of the cochlear once implantation is complete.

SUMMARY

In one aspect of the present invention, an electrode assembly for implantation in a recipient's cochlear via a cochleostomy is disclosed. The electrode assembly comprises an electrode array and an elongate carrier member having a lumen extending longitudinally through at least a portion thereof, and having a distal end on which said electrode array is disposed. The elongate carrier member comprises a distal intra-cochlear region adapted to be implanted in the cochlear, and having the lumen extending at least partially therethrough; and an incision region, contiguous with the intra-cochlear region, adapted to be partially positioned in the cochlear, wherein the lumen extending therethrough is non-communicative across the cochleostomy.

In another aspect of invention, a prosthetic hearing implant system is disclosed. The prosthetic hearing implant system comprises an electrode assembly for implantation in a recipient's cochlear via a cochleostomy. The electrode assembly comprises an electrode array and an elongate carrier member having a lumen extending longitudinally through at least a portion thereof, and having a distal end on which the electrode array is disposed. The elongate carrier member comprises a distal intra-cochlear region adapted to be implanted in the cochlear, and having the lumen extending at least partially therethrough; and an incision region, contiguous with the intra-cochlear region, adapted to be partially positioned in the cochlear, wherein the lumen extending therethrough is non-communicative across the cochleostomy.

In a further aspect of the invention, an electrode assembly for implantation in a recipient's cochlear via a cochleostomy is disclosed. The electrode assembly comprises: an elongate stylet; an electrode array; and an elongate carrier member having a distal end on which said electrode array is disposed, comprising: a distal intra-cochlear region adapted to be implanted in the cochlear and having a lumen extending at least partially therethrough; and an incision region, contiguous with the intra-cochlear region, adapted to be partially positioned in the cochlear, having a non-communicative extending therethrough; and an elongate cartridge configured to slidingly receive said stylet and said carrier member.

BRIEF DESCRIPTION OF THE DRAWINGS

Embodiments of the present invention are described herein in conjunction with the accompanying drawings, in which:

FIG. 7 is a side view of an electrode assembly in accordance with one embodiment of the present invention;

FIG. 8A is a side view of an electrode assembly in accordance with one embodiment of the present invention;

FIG. 8B is a cross-sectional view of the electrode assembly illustrated in FIG. 8A taken along section line 8B-8B;

FIG. 8C is a cross-sectional view of the electrode assembly illustrated in FIG. 8A taken along section line 8C-8C in FIG. 8A;

FIG. 10 is a perspective view of an electrode assembly in accordance with one embodiment of the present invention;

FIG. 11 is a perspective view of an electrode assembly in accordance with one embodiment of the present invention;

DETAILED DESCRIPTION

Aspects of the present invention are directed to an implantable elongate carrier member, lead, catheter or the like (collectively and generally referred to as a "carrier member") with an integrated lumen and a therapeutic device disposed at the distal end of the carrier member. Lumens which pass through an incision made to implant a therapeutic device create a potential pathway for fluids, tissue, cells, bacteria or other organic material which may, for example, damage the therapeutic device or cause infection, disease or other undesirable medical conditions. For example, in the context of a cochlear implant, a carrier member lumen that extends through a cochleostomy may increase the risk of meningitis caused by fluid ingress into the lumen and, ultimately, into the cochlear.

Aspects of the present invention provide a carrier member lumen that is non-communicative across the incision to prevent the lumen from serving as a communicative pathway for organic material through the incision. In various embodiments of the present invention, the non-communicative lumen is severed, removed, blocked, diverted or otherwise interrupted in the region of the carrier which transitions through the incision thereby interrupting the pathway for the organic material.

Exemplary embodiments of the present invention are further described below in conjunction with an implanted unit of a prosthetic hearing implant system, such as a Contour™, Freedom™, Nucleus™ or Cochlear™ systems commercially available from Cochlear Limited, Australia. Such devices are described in U.S. Pat. Nos. 4,532,930, 6,537,200, 6,565,503, 6,575,894, and 6,697,674, the entire contents and disclosures of which are hereby incorporated by reference herein. It should be understood to those of ordinary skill in the art that embodiments of the present invention may be used in other stimulating medical devices such as neurostimulators, cardiac pacemakers/defibrillators, etc.

Figure 1:
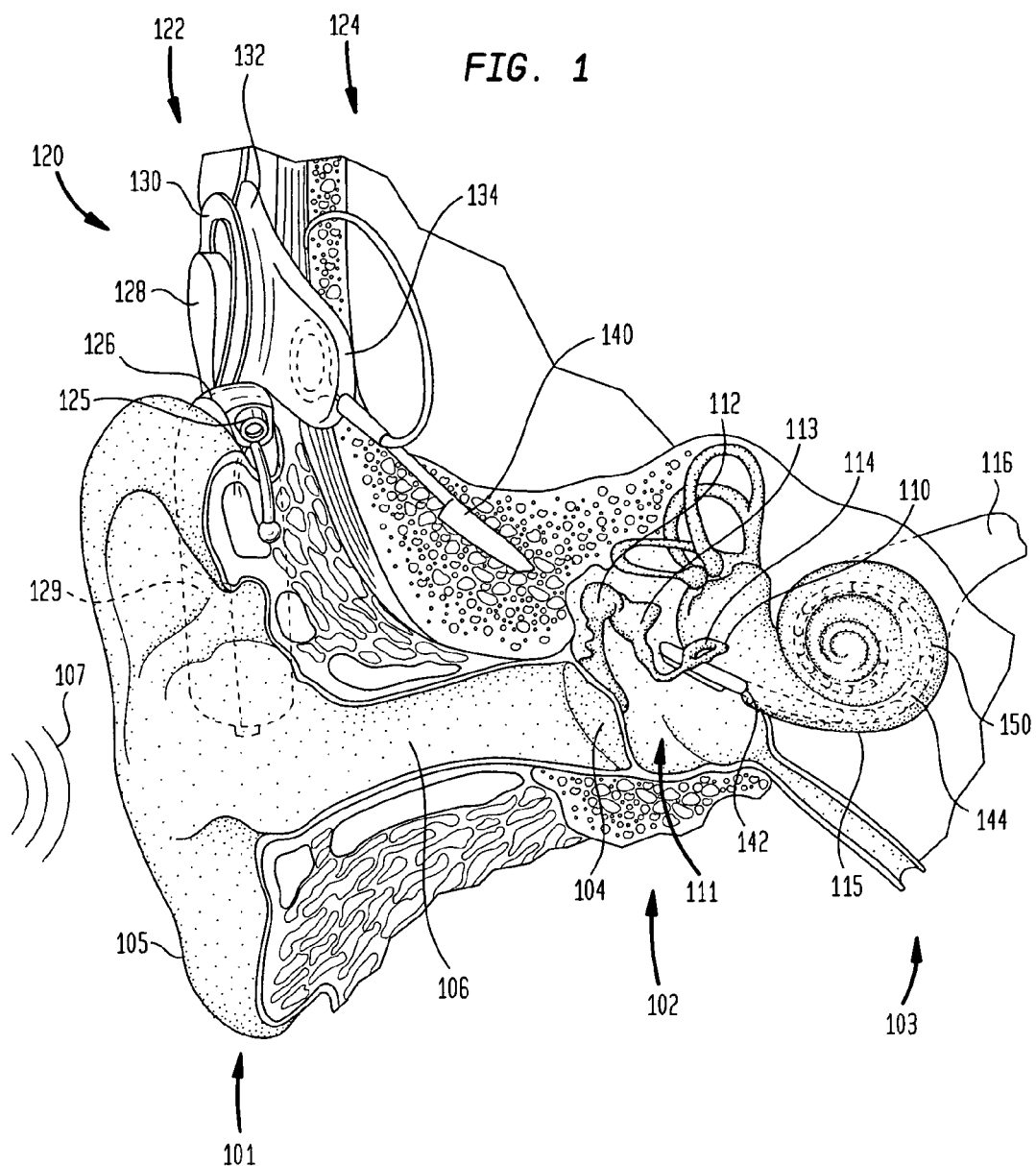
FIG. 1 is a perspective view of an implanted prosthetic hearing implant system having a non-communicative lumen in accordance with embodiments of the present invention.

FIG. 1 is a cut-away view of the relevant components of outer ear 101, middle ear 102 and inner ear 103, which are described next below. In a fully functional ear, outer ear 101 comprises an auricle 105 and an ear canal 106. An acoustic pressure or sound wave 107 is collected by auricle 105 and channeled into and through ear canal 106. Disposed across the distal end of ear cannel 106 is a tympanic membrane 109 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In deaf persons, there is an absence or destruction of the hair cells. Prosthetic hearing implant 120 is needed to directly stimulate the ganglion cells to provide a hearing sensation to the recipient.

FIG. 1 also shows how an implanted prosthetic hearing implant 120 is positioned in relation to outer ear 101, middle ear 102 and inner ear 103. Prosthetic hearing implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is outputted to a BTE (Behind-The-Ear) speech processing unit 126 that generates coded signals and are provided to an external transmitter unit 128, along with power from a power source 129 such as a battery. External transmitter unit 128 comprises an external coil 130 and, preferably, a magnet (not shown) secured directly or indirectly in external coil 130. Internal components 124 comprise an internal receiver unit 132 having an internal coil (not shown) that receives and transmits power and coded signals from external assembly 122 to a stimulator unit 134 to apply the coded signal along an electrode assembly 140. Electrode assembly 140 enters cochlea 115 at cochleostomy region 142 and has one or more electrodes 150 is positioned to substantially be aligned with portions of tonotopically-mapped cochlea 115. Signals generated by stimulator unit 134 are applied by the electrodes 150 of electrode array 144 to cochlea 115, thereby stimulating the auditory nerve 116. It should be appreciated that although in the embodiment shown in FIG. 1 electrodes 150 are arranged in an array 144, other arrangements are possible.

Figure 2A:
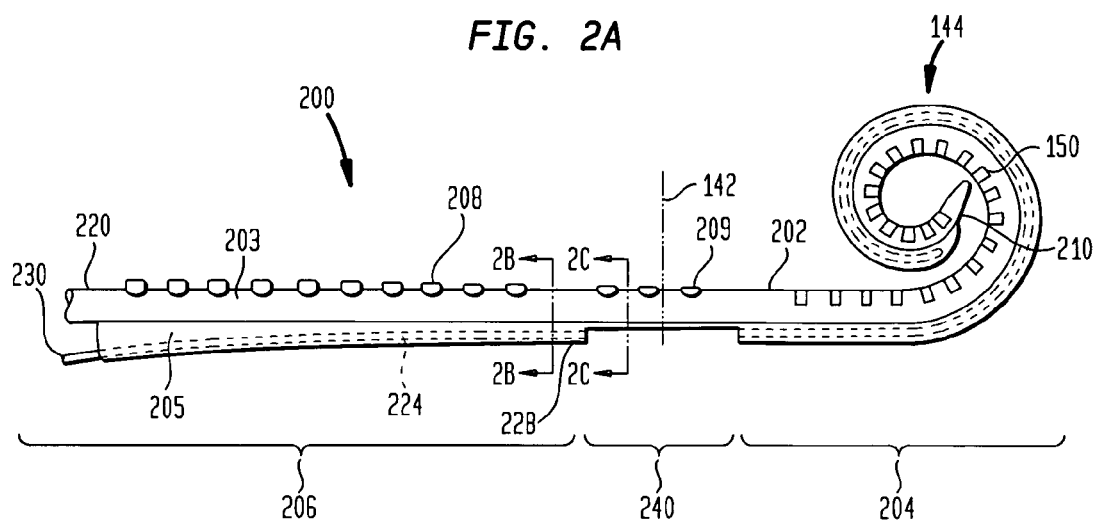
FIG. 2A is a side view of an electrode of assembly in accordance with one embodiment of the present invention.
Figure 2B:
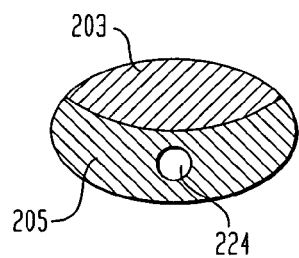
FIG. 2B is a cross-sectional view of one embodiment of the of the electrode assembly illustrated in FIG. 2A taken along section line 2B-2B in FIG. 2A.
Figure 2C:
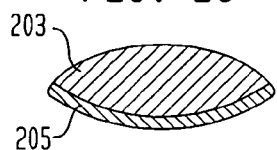
FIG. 2C is a cross-sectional view of one embodiment of the electrode assembly illustrated in FIG. 2A taken along section line 2C-2C in FIG. 2A.

FIGS. 2A through 2C are side and cross-sectional views, respectively, of one embodiment of electrode assembly 140 illustrated in FIG. 1, referred to herein as electrode assembly 200. Electrode assembly 200 has an elongate carrier member 202 on which an array 144 of electrodes 150 is disposed. Electrode assembly 200 and, hence, carrier member 202, has a distal end 210 at which electrode array 144 is disposed, and a proximal end 220 which either is connected to, or is proximate to, stimulator unit 134 (not shown in FIG. 2A). For ease of description, future reference to a carrier member and an electrode assembly are considered to refer to the other unless otherwise understood from the context or express statements.

This illustrative embodiment of electrode assembly 200 comprises three contiguous regions: an intra-cochlear carrier region 204 disposed toward and comprising distal end 210 of electrode assembly 200, an extra-cochlear carrier region 206 disposed toward and comprising proximal end 220 of electrode assembly 200, and an incision region 240 interposed between intra-cochlear carrier region 204 and extra-cochlear carrier region 206.

In the exemplary cochlear implant application, the incision made to implant an electrode assembly such as electrode assembly 140 is commonly referred to as a cochleostomy. For example, in the above description referring to FIG. 1, the incision in cochlear 115 is referred to as cochleostomy region 142 or, simply, cochleostomy 142. The location of cochleostomy 142 is schematically represented in FIG. 2A by a dashed line. As one of ordinary skill in the art would appreciate, dashed line 142 represents the common general location of the cochleostomy; it does not represent other aspects of the cochleostomy such as, for example, the thickness of the incision.

Electrode assembly 200 is configured such that, when implanted, the portion of elongate electrode assembly 200 located in cochlear 115 includes intra-cochlear carrier region 204 and a portion of incision region 240. As such, the remaining portion of incision region 240 and extra-cochlear carrier region 206 are located external to cochlear 115 when carrier member 200 is implanted.

Electrode assembly 200 further comprises a lumen 224 extending through a substantial length of elongate carrier member 202. Lumen 224 extends through a portion of extra-cochlear carrier region 206 and a portion of intra-cochlear carrier region 204. In accordance with the teachings of the present invention, at least the section of incision region 240 that extends through cochleostomy 142 is non-communicative. As such, there is no communication of organic material from the portion of the lumen external to cochlear 115 to the portion of the lumen internal to cochlear 115. Notably, in the embodiment shown in FIG. 2A, lumen 224 is interrupted or absent in incision region 240, as shown in FIG. 2A. This is described in further detail below with reference to FIGS. 2B and 2C. FIG. 2B is a cross-sectional view of carrier member 200 taken along section line 2B-2B through extra-cochlear region 206 as shown in FIG. 2A; FIG. 2C is a cross-sectional view of carrier member 200 taken along section line 2C-2C through incision region 240 as shown in FIG. 2A.

Carrier member 202 may be further considered to have an upper elongate region 203 and a lower elongate region 205. As shown in FIGS. 2A and 2B, intra- and extra-cochlear regions 204 and 206 comprise both upper and lower elongate regions 203 and 205, while incision region 240 comprises upper elongate region 203 and only a small portion of lower elongate region 205. Lower elongate region 205 in incision region 240 does not include any portion of lumen 224. As such, the cross-sectional area of electrode assembly 200 in incision region 240 is less than the cross-sectional area of electrode assembly 200 in extra-cochlear region 206, and lumen 224 extends through extra- and intra-cochlear regions 206 and 204, and is absent in incision region 240. More generally, lumen 224 in region 240 of carrier 200 extending through incision 142 is interrupted to prevent lumen 224 from serving as a communicative pathway for organic material or other undesirable material through the incision. In other words, lumen 224 is a non-communicative lumen due to the absence of lumen 224 in incision region 240.

Lumen 224 is configured to receive a straightening element 230 such as a wire, which is commonly referred to as a stylet in the context of prosthesis hearing implant systems. Regardless of application, straightening elements described herein in connection with various embodiments of the present invention are referred to herein as stylets for ease of reference. Prior to implanting electrode assembly 200, stylet 230 is inserted into lumen 224 to straighten electrode assembly 200, which is biased to curl; that is, to have an approximately round shape formed by one or more concentric circles. Thus, in intra-cochlear carrier region 204, lumen 224 performs a straightening function that holds electrode assembly 200 substantially straight during insertion. While electrode assembly 200 is inserted through cochleostomy 142, a surgeon biases forward carrier member 202 on stylet 230 to implant carrier member 202, causing carrier member 202 to curve so as to follow the curvature of cochlear 115.

Carrier member 202 may have a series of one or more optional guide ribs 208 disposed on the surface of extra-cochlear region 206 to facilitate manual control (direct or with an instrument) of carrier member 202 during implantation. In one embodiment, guide ribs 208 extend around a portion of the circumference of carrier member 200 and are raised above surface of carrier member 202 as shown in FIG. 2A. As one of ordinary skill in the art would find apparent, guide ribs are not required, and when utilized in various embodiments of the present invention, may take on other forms suitable for facilitating manual or instrument control of the carrier member.

Carrier member 202 also has a series of one or more optional markers 209 disposed in or on incision region 240 of carrier member 200. In the embodiment shown in FIG. 2A, there are three markers 209 embedded in the surface of carrier member 200. Markers 209 facilitate locating carrier member 200 such that incision region 240 is positioned so as to be partially located within cochlear 115. As one of ordinary skill in the art would appreciate, markers 209 as well as other markers implemented in other embodiments of the present invention may be any type of device that facilitates visual recognition of the location of the carrier member in a recipient. Such recognition may involve imaging systems in which case one or more of the markers 209 will include features or materials identifiable by such imaging systems.

Lumen 224 in extra-cochlear carrier region 206 performs a guiding function rather than a straightening function since carrier member 202 is straight (not pre-curved) in this region of electrode assembly 200. Such guiding function in lumen 224, and hence extra-cochlear region 206 of electrode assembly 200, may provide a point to hold electrode assembly 200 and stylet 230 well away from cochlea 115 and outside the posterior tympanotomy.

During the packing of cochleostomy area 142 with temporalis fascia, the fascia presses and hermetically seals against carrier member 202. Other techniques to seal and hold electrode assembly 202 in cochleostomy region 142 may be used instead of or in addition to packing, such as the use of sutures or split bridge.

There are a number of advantages which may be derived from the above embodiments of the present invention. For example, electrode assembly 200 may be inserted and manipulated in a manner that is substantially similar to techniques commonly used to implant a conventional electrode assembly; that is, one having a continuous lumen. Thus no new training is required for surgeons utilizing embodiments of the present invention. Further, the embodiments shown in FIGS. 2A through 2C may provide additional benefits over standard electrode assemblies in that the contacting area between carrier member 202 and stylet 230 is reduced. The reduced contact area may, in turn, reduce the dynamic friction between the carrier member and stylet, thereby reducing the force required to remove stylet 230 from carrier member 202. Also, the reduction in friction may decrease the propensity for stylet 230 to temporarily adhere to carrier member 202 when electrode assembly 200 is installed on and removed from stylet 230.

Figure 3A:
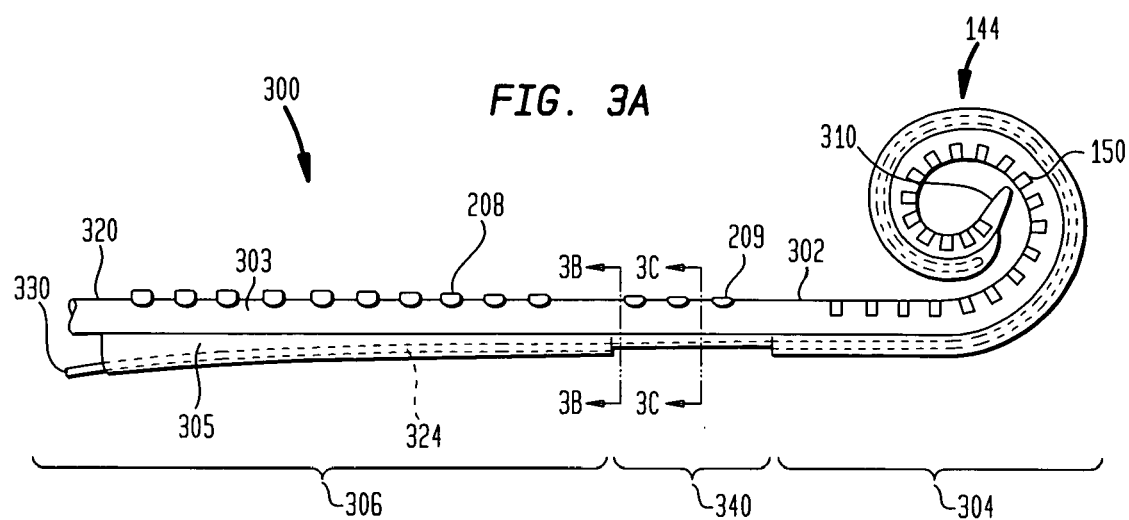
FIG. 3A is a side view of an electrode assembly in accordance with one embodiment of the present invention.
Figure 3B:
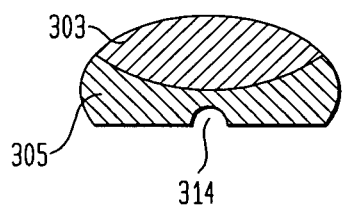
FIG. 3B is a cross-section view of one embodiment of the electrode assembly shown FIG. 3A, taken along section line 3B-3B in FIG. 3A.

FIGS. 3A and 3B illustrate another embodiment of electrode assembly 140 of the present invention, referred to herein as electrode assembly 300. FIG. 3A is a side view of electrode assembly 300 while FIG. 3B is a cross-section view of electrode assembly 300 taken along section line 3B-3B in FIG. 3A.

Figure 3C:
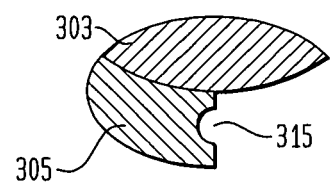
FIG. 3C is a cross-section view of an alternative embodiment of the electrode assembly shown in FIG. 3A, also taken along section line 3C-3C in FIG. 3A.

In the embodiment illustrated in FIGS. 3A-3B, lower elongate region 305 of carrier member 302 is partially removed in incision region 340. As shown best in FIG. 3B, the portion of lower elongate region 305 that is not removed defines an upper surface 314 of lumen 324. That is, lumen 324 is non-communicative in incision region 340 due to the partial removal of lumen 324 in that region. It should be appreciated that the partial removal of lumen 324 sufficient to make lumen 324 non-communicative may vary depending on the particular objectives and applications. For example, in the alternative embodiment illustrated in FIG. 3C, the remaining portion of lower elongate region 305 defines a side surface 315 of lumen 324. As such, this embodiment of lumen 324 is also non-communicative in incision region 340 due to the partial removal of lumen 324 in that region. As one of ordinary skill in the art would appreciate, other portions of lower elongate region 305 of carrier member 302 may be removed or otherwise altered to make lumen 324 non-communicative in incision region 340 region.

Figure 4:
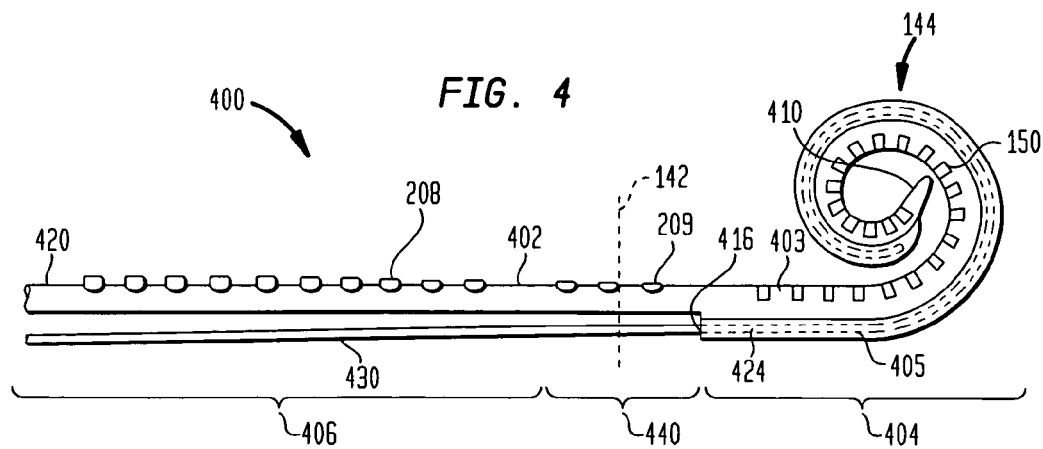
FIG. 4 is a side view of an electrode assembly in accordance with one embodiment of the present invention.

FIG. 4 is a side view of another embodiment of electrode assembly 140 introduced above with reference to FIG. 1, referred to herein as electrode assembly 400. The illustrative embodiment of electrode assembly 400 illustrated in FIG. 4 comprises three contiguous regions: an intra-cochlear carrier region 404 disposed toward and comprising distal end 410 of electrode array 400, an extra-cochlear carrier region 406 disposed toward and comprising proximal end 420 of electrode assembly 400, and an incision region 440 interposed between intra-cochlear carrier region 404 and extra-cochlear carrier region 406.

In addition, electrode assembly 400 is formed of two integrated or unitary elongate portions: an upper elongate portion 403 and a lower elongate portion 405. As shown in FIG. 4, lower elongate portion 405 of carrier member 402 is removed from extra-cochlear carrier region 404 and incision region 440. As such, lumen 424 extend through a portion of intra-cochlear region 404 and neither cochleostomy region 142 nor extra-cochlear carrier region 406. Lumen 424 has a proximal opening 416 configured to receive stylet 430, as shown in FIG. 4. Thus, there is no communicative path through incision region 142 via lumen 424. During the packing of cochleostomy area 142, the fascia presses and hermetically seals against electrode assembly 400.

It is noted that intra-cochlear carrier region 404 performs guiding and straightening functions toward distal end 410 which allows electrode assembly 400 to be pushed forward on stylet 430. This may improve the precision with which electrode assembly 400 is controlled during implantation since the pushing of stylet 430 may occur at a location closer to distal end 410 of electrode assembly 400.

Since there is no carrier or lumen in cochleostomy region 142, a weak point may be created in electrode assembly 400. The weak point may lead to undesirable bending or kinking should electrode assembly 400 meet resistance during implantation. Therefore, in certain embodiments of electrode assembly 400 carrier member 402 is strengthened in cochleostomy region 440.

As noted above with reference to the embodiments illustrated in FIGS. 2A-2C, the contacting area between carrier member 402 and stylet 430 is reduced. This reduced contact area may, in turn, reduce the dynamic friction between the carrier member and stylet, thereby reducing the force required to remove stylet 430 from carrier member 402. Also as noted above, the reduction in friction may decrease the propensity for stylet 430 to temporarily adhere to carrier member 402 when electrode assembly 400 is installed on and removed from stylet 430.

Figure 5A:
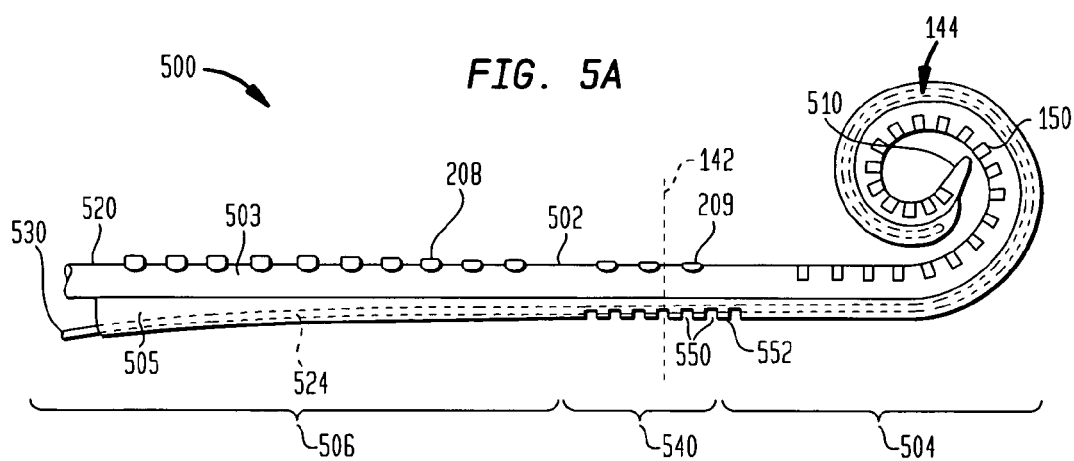
FIG. 5A is a side view of an electrode assembly in accordance with one embodiment of the present invention.
Figure 5B:
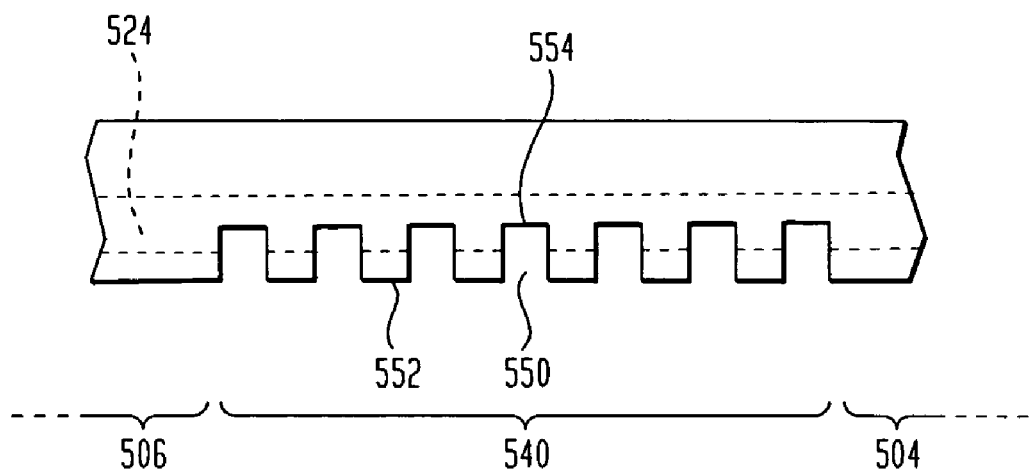
FIG. 5B is an enlarged side view of one embodiment of the electrode assembly incision region shown in FIG. 5A.
Figure 5C:
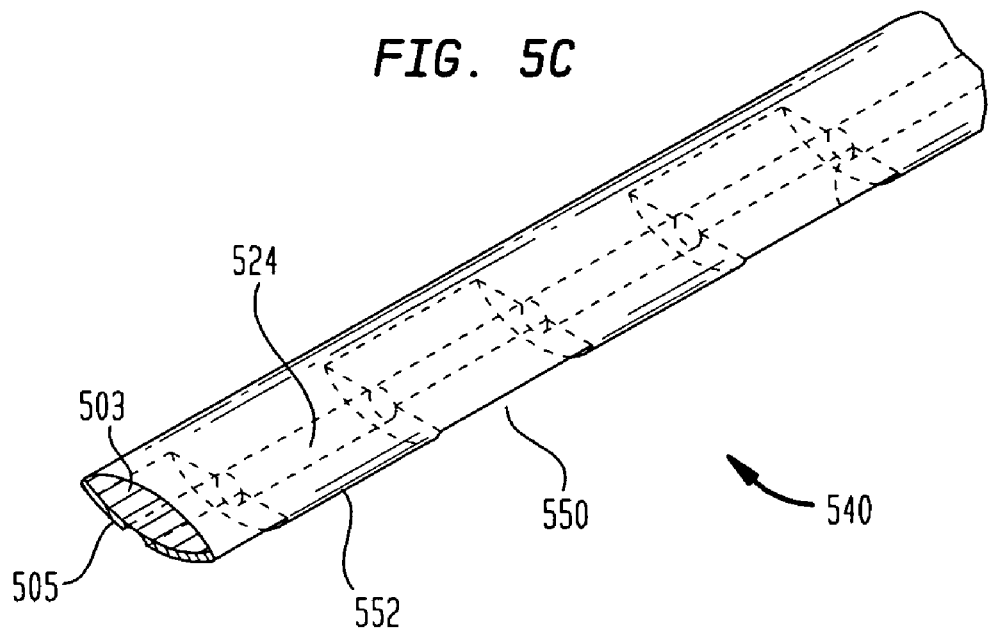
FIG. 5C is a perspective view of one embodiment of the electrode assembly incision region shown in FIG. 5A.

FIGS. 5A, 5B and 5C illustrate another embodiment of an electrode assembly 140 having a non-communicative lumen in accordance with the teachings of the present invention, referred to herein as electrode assembly 500. FIG. 5A is a side view of electrode assembly 500. Electrode assembly 500 has a carrier member 502 formed of an upper elongate portion 503 and a lower elongate portion 505. Electrode assembly 500 comprises three contiguous regions: an intra-cochlear carrier region 504 disposed toward and comprising distal end 510 of electrode array 500, an extra-cochlear carrier region 506 disposed toward and comprising proximal end 520 of electrode assembly 500, and an incision region 540 interposed between intra-cochlear carrier region 504 and extra-cochlear carrier region 506. FIG. 5B is an enlarged side view and FIG. 5C is a perspective view of incision carrier region 540 of FIG. 5A.

Lumen 524 extends through at least a portion of intra-cochlear region 504, incision region 540 and extra-cochlear carrier region 506. In FIG. 5A a stylet 530 is shown partially inserted into lumen 524.

A series of one or more radial slots 550 are formed in lower elongate portion 505 of carrier member 502 in incision region 142 of electrode assembly 500. In the embodiment shown in FIG. 5A, there are a plurality of radial slots 550 and a plurality of radial support ribs 552. Radial slots 550 interrupt lumen 524, resulting in a lumen which is non-communicative at a number of locations in incision region 540. That is, radial slots 550 ensure that there is no continuous pathway for organic material or other undesirable elements to travel through lumen 524 through cochleostomy 142.

Radial support ribs 552 provide further guiding and straightening functions that assist in constraining stylet 530 during insertion and withdrawal. Radial support ribs 552 also allow markers 209 to extend up to approximately 270° degrees around the circumference of electrode assembly 500.

In one embodiment, radial support ribs 552 are approximately 0.2 to 1 mm in length, and radial slots 550 are approximately 0.2 mm to 1 mm in length. In one particular embodiment, radial extensions 552 are 0.5 mm in length and radial slots 550 are 0.5 mm. In the illustrative embodiment, radial slots 550 have similar dimensions while radial extensions 552 have similar dimensions. It should be appreciated, however, that in alternative embodiments, a different quantity of radial slots 550 have dimensions which are the same or different than the dimensions of radial extensions 552 and those illustrated in FIGS. 5A-5C may be implemented. It should also be appreciated that in those embodiments in which there is a plurality of radial slots 550 and radial support ribs 552, the dimensions of such radial slots and support ribs may vary along the length of incision region 540.

Figure 6A:
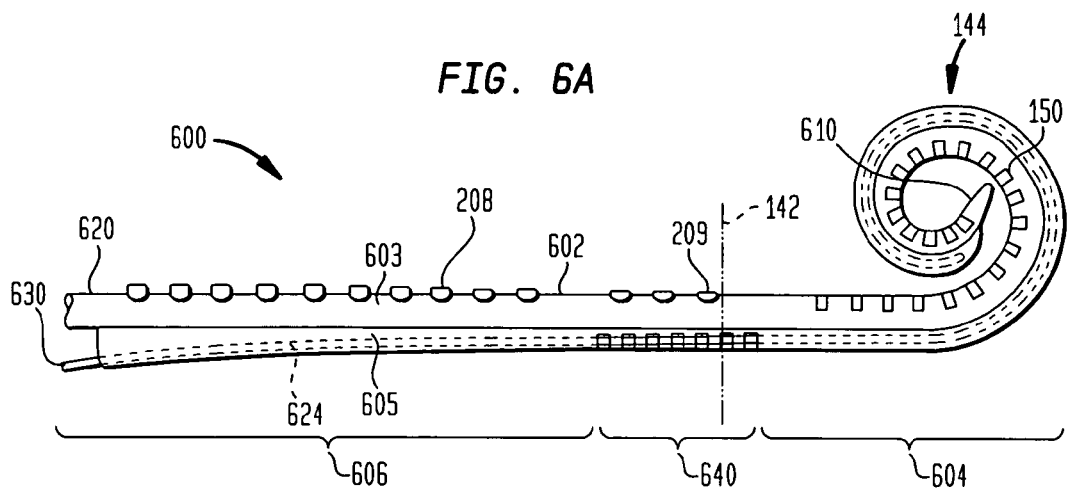
FIG. 6A is a side view of an electrode assembly in accordance with one embodiment of the present invention.
Figure 6B:
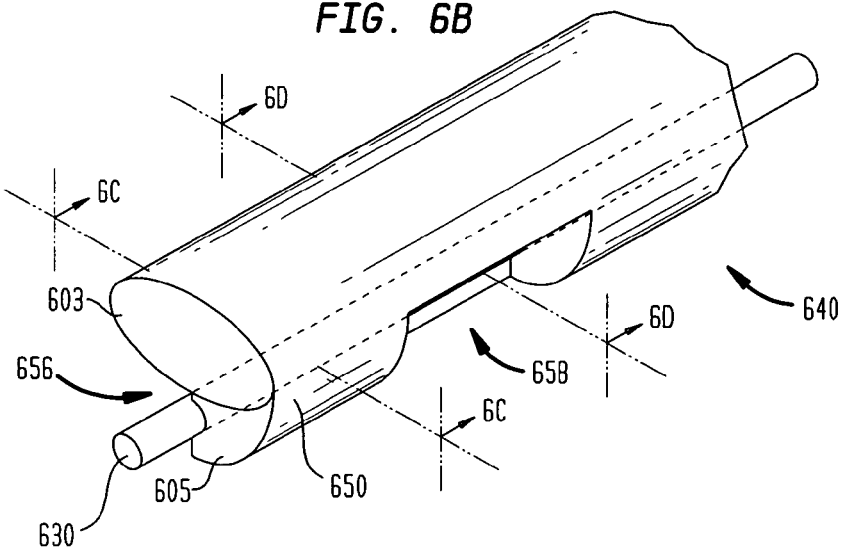
FIG. 6B is a perspective view of the incision region of the electrode assembly illustrated in FIG. 6A.
Figure 6C:
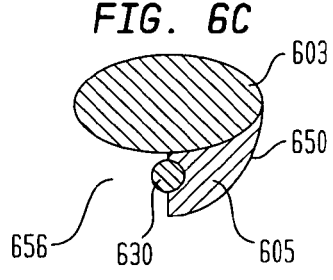
FIG. 6C is a cross-sectional view of the incision region of the electrode assembly illustrated in FIGS. 6A and 6B taken along section line 6C-6C in FIG. 6B.
Figure 6D:
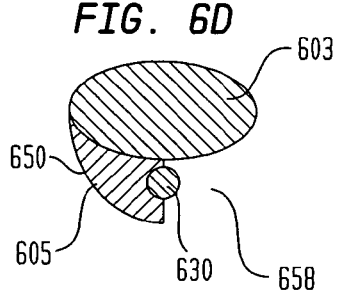
FIG. 6D is a cross-sectional view of the incision region of the electrode assembly illustrated in FIGS. 6A and 6B taken along section line 6D-6D in FIG. 6B.

FIGS. 6A through 6D illustrate another embodiment of an electrode assembly 140 having a non-communicative lumen in accordance with the teachings of the present invention, referred to herein as electrode assembly 600. FIG. 6A is a side view of electrode assembly 600. Electrode assembly 600 has a carrier member 602 formed of an upper elongate portion 603 and a lower elongate portion 605. Electrode assembly 600 comprises three contiguous regions: an intra-cochlear carrier region 604 disposed toward and comprising distal end 610 of electrode array 600, an extra-cochlear carrier region 606 disposed toward and comprising proximal end 620 of electrode assembly 600, and an incision region 640 interposed between intra-cochlear carrier region 604 and extra-cochlear carrier region 606. FIG. 6B is a perspective view, and FIGS. 6C and 6D are cross-sectional views taken along section lines 6C-6C and 6D-6D, respectively, of incision carrier region 640, as shown in FIG 6B.

Lumen 624 extends through at least a portion of intra-cochlear region 604, incision region 640 and extra-cochlear carrier region 606. A stylet 630 is shown positioned within lumen 624. In incision region 640, lower elongate region 605 comprises a series of sequentially alternating lateral support ribs 650. That is, in one portion of incision region 640, a lateral support rib 650 laterally supports stylet 630 from one side of carrier member 602, and in a linearly adjacent portion of incision region 640, a neighboring lateral support rib 650 laterally supports stylet 630 from the laterally-opposing side of carrier member 602.

This is illustrated in FIGS. 6C and 6D which are cross-sectional views of incision region 640 taken along section lines A-A and B-B in FIG. 6B. In particular, FIGS. 6C and 6D are cross-sectional views showing linearly adjacent lateral support ribs 650 in incision region 640. As shown in FIGS. 6B and 6C, lateral support rib 650 at section line 6C-6C laterally supports stylet 630 on one side of the stylet. The laterally opposite side of lower elongate region 605 is a void 656. Conversely, as shown in FIGS. 6B and 6D, lateral support rib 650 at section line 6D-6D laterally supports stylet 630 on the opposing side of the stylet. The other side of lower elongate region 605 is a void 656. Thus, stylet 630 is supported in lumen 624 along incision region 640 by alternating lateral support ribs 650. The alternating design creates a lumen 624 having a non-communicative pathway in incision region 640 of electrode assembly 600.

Lateral support ribs 650 provide further guiding and straightening functions that assist in constraining stylet 630 during withdrawal. Lateral support ribs 650 also allow markers 209 to extend up to approximately 270° degrees around the circumference of electrode assembly 600 in incision region 640.

FIG. 7 is a side view of another embodiment of electrode assembly 140 having a non-communicative lumen in accordance with the teachings of the present invention, referred to herein as electrode assembly 700. Electrode assembly 700 has a carrier member 702 formed of an upper elongate portion 703 and a lower elongate portion 705. Electrode assembly 700 comprises three contiguous regions: an intra-cochlear carrier region 704 disposed toward and comprising distal end 710 of electrode array 700, an extra-cochlear carrier region 706 disposed toward and comprising proximal end 720 of electrode assembly 700, and an incision region 740 interposed between intra-cochlear carrier region 704 and extra-cochlear carrier region 706.

Lumen 724 extends through at least a portion of intra-cochlear region 704, incision region 740 and extra-cochlear carrier region 706. A stylet 730 is shown positioned within lumen 724. The portion of lumen 724 extending through intra-cochlear region 704 performs a straightening and guiding function while the portion of lumen 724 extending through extra-cochlear region 706 performs a guiding function.

A section 788 of lower elongate portion 705 of carrier member 702 in incision region 740 is removable. Upon removal of removable section 788 from lower elongate portion 705, lumen 724 will be interrupted in incision region 740, resulting in a non-communicative lumen 724 across incision 142.

In one embodiment, removable section 788 of lower elongate portion 705 is formed from a dissolvable/resorbable material. For example, in certain embodiments, removable section 788 is formed of a resorbable polymer such as polylactic acid (PLA) and polyglycolic acid (PGA). Other biodegradable or dissolvable materials or combinations thereof may be used as well. After insertion of electrode assembly 700 and packing of cochleostomy 142, the resorbable polymer is absorbed by the recipient, resulting in a non-communicative lumen 124 across incision 142. Advantageously, removable section 788 provides for a non-communicative lumen 724 in incision region 740 when electrode assembly 700 is implanted while also enhancing the strength of electrode assembly 700 during implantation.

Alternatively, section 788 is a detachable section of lower elongate portion 705 in an alternative embodiment of the present invention. In such alternative embodiments, section 788 is removed manually or otherwise prior to implantation or packing of cochleostomy area 142. In one embodiment, section 788 is configured to be easily removable with forceps.

FIG. 8A is a side view of another embodiment of electrode assembly 140 having a non-communicative lumen in accordance with the teachings of the present invention, referred to herein as electrode assembly 800. Electrode assembly 800 has a carrier member 802 formed of an upper elongate portion 803 and a lower elongate portion 805. Electrode assembly 800 comprises three contiguous regions: an intra-cochlear carrier region 804 disposed toward and comprising distal end 810 of electrode array 800, an extra-cochlear carrier region 806 disposed toward and comprising proximal end 820 of electrode assembly 800, and an incision region 840 interposed between intra-cochlear carrier region 804 and extra-cochlear carrier region 806.

Lumen 824 extends through at least a portion of intra-cochlear region 804, incision region 840 and extra-cochlear carrier region 806. In this embodiment, lumen 824 is a collapsible lumen that expands in response to an insertion force applied to stylet 830. FIG. 8A is a cross-sectional view of carrier member 802 taken along section line 8B-8B of FIG. 8A. As shown in FIGS. 8A and 8B, collapsible lumen 824 is forced open and extends around the circumference of the inserted portion of stylet 830.

FIG. 8C is a cross-sectional view of carrier member 802 taken along section line 8C-8C of FIG. 8A. As shown in FIG. 8A, stylet 830 does not extend through lumen 824 to section line 8C-8C. As such, lumen 824 is collapsed at section line 8C-8C, as shown in FIG. 8C. Thus, lumen 824 expands and collapses in response to the introduction and presence of stylet 830. Prior to implantation, stylet 830 is inserted into collapsed lumen 824, causing lumen 824 to expand around stylet 830. Then, electrode assembly 800 is implanted during which stylet 830 is removed from lumen 824. As stylet 830 is removed, lumen 824 collapses once again, resulting in a non-communicative lumen. In such embodiments, lumen 824 is non-communicative along its entire length as compared to certain other embodiments of the present invention in which lumen 824 is non-communicative only in incision region 142.

In addition, packing lumen 824 will further compress and creates a seal and a non-communicative path in lumen 824. During the packing of cochleostomy 142, the fascia presses and hermetically seals against electrode assembly 800. Lumen 824 may also be plugged with a plugging material (not shown) once stylet 830 is fully removed. As one of ordinary skill in the art would appreciate, in such embodiments carrier member 802 performs guiding and straightening functions throughout its entire length.

Figure 9:
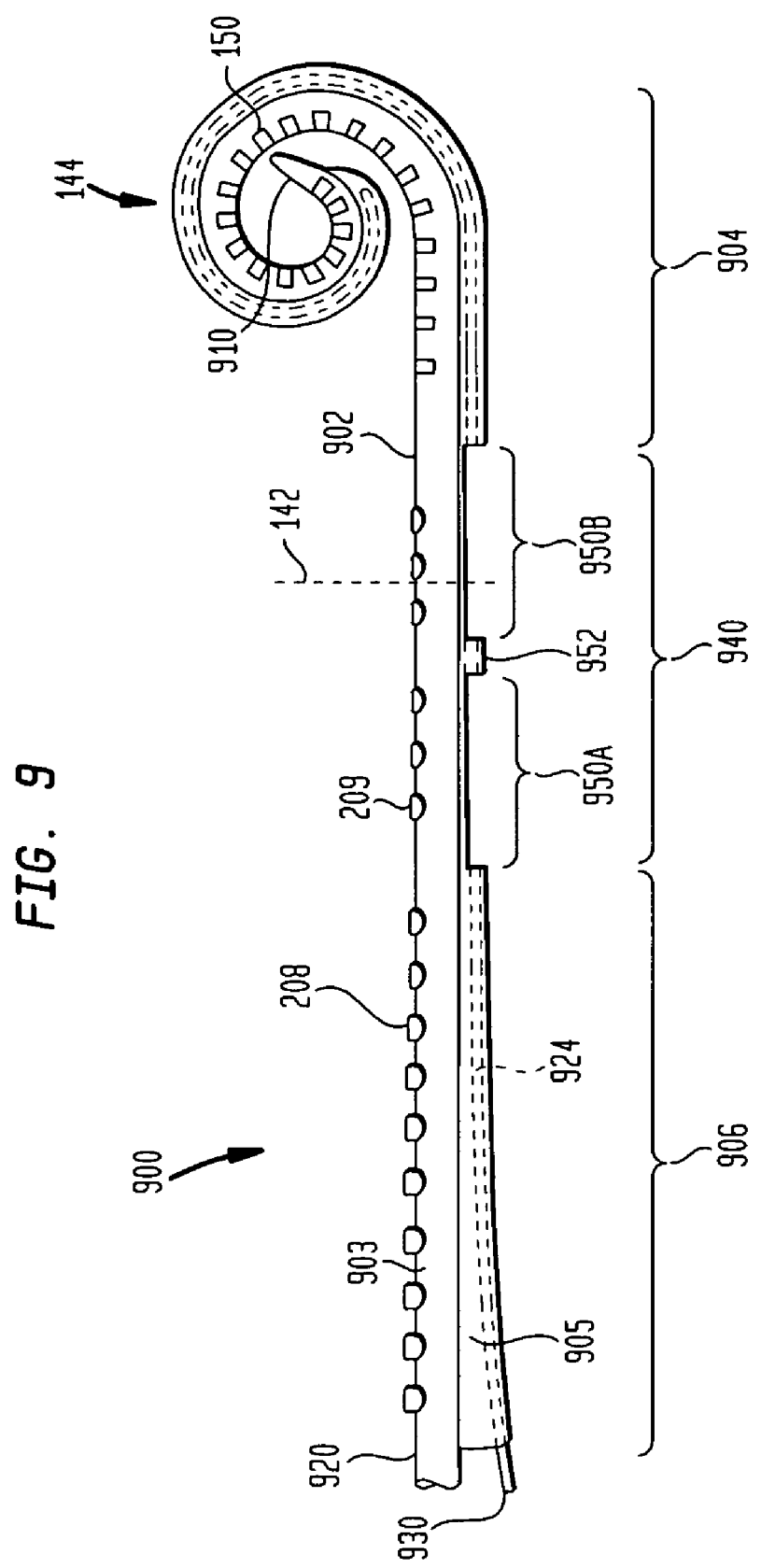
FIG. 9 is a side view of an electrode assembly in accordance with one embodiment of the present invention.

FIG. 9 is a side view of another embodiment of electrode assembly 140 having a non-communicative lumen in accordance with the teachings of the present invention, referred to herein as electrode assembly 900. Electrode assembly 900 has a carrier member 902 formed of an upper elongate portion 903 and a lower elongate portion 905. Electrode assembly 900 comprises three contiguous regions: an intra-cochlear carrier region 904 disposed toward and comprising distal end 910 of electrode array 900, an extra-cochlear carrier region 906 disposed toward and comprising proximal end 920 of electrode assembly 900, and an incision region 940 interposed between intra-cochlear carrier region 904 and extra-cochlear carrier region 906.

Lumen 924 extends through at least a portion of intra-cochlear region 904, incision region 940 and extra-cochlear carrier region 906. In this embodiment, lumen 924 is interrupted along two sections 950A and 950B in incision region 940. Section 950A and 950B are divided by a support rib 952. In the illustrative embodiment, such interruption is attained by the absence of lower elongate portion 905 of carrier member 902. Advantageously, this allows electrode assembly 900 to be positioned at different depths to account for the various depth requirements of electrode assembly 900.

FIGS. 10 and 11 are perspective views of two embodiments of an electrode assembly 140 having a non-communicative lumen in accordance with the teachings of the present invention, referred to herein as electrode assembly 1000 and 1100, respectively. Electrode assemblies 1000 and 1100 each comprises three contiguous regions similar to those described above in connection with other embodiments of the present invention. In FIGS. 10 and 11 only a portion of incision region 1040 and 1140, respectively, are shown for clarity.

Electrode assembly 1000 has a carrier member 1002 formed of an upper elongate portion 1003 and a lower elongate portion 1005. Similarly, electrode assembly 1100 has a carrier member 1102 formed of an upper elongate portion 1103 and a lower elongate portion 1105.

Carrier members 1002 and 1102 each have a raised surface 1007 and 1107, respectively, formed on upper elongate portion 1003 and 1 103, in incision region 1004 and 1104, respectively. Raised surfaces 1007 and 1107 are provided in addition or alternatively to markers 209 described above in connection with other embodiments of the present invention. A removable cartridge 1080 and 1180 travels parallel with the longitudinal axis of the respective carrier members 1002 and 1102 on rails 1070, 1170 formed in the upper elongate portions 1005, 1105, respectively.

In both embodiments, stylets 1030, 1130 extend through the respective lumen 1024, 1124 that is provided in extra-cochlear region (not shown) and intra-cochlear region 1004, 1104, respectively. In incision regions 1040 and 1140, lower elongate portions 1005 and 1105 are at least partially absent to provide a non-communicative lumen in incision regions 1040 and 1140. In the embodiment shown in FIG. 10, lower elongate portion 1005 is completely absent while in the embodiment shown in FIG. 11, lower elongate portion 1105 is partially absent.

In both embodiments, upper elongate portions 1005 and 1105 form a rail adapted to be slidingly received by slots 1082 and 1182, respectively, of their respective cartridge 1080 and 1180. Removal cartridges 1080 and 1180 may slide or fit over rails 1070 and 1170 as shown in FIGS. 10 and 11. Further, removal cartridges 1080 and 1180 may be connected to the respective stylet 1030 and 1130 to enable the surgeon to guide the stylet out of the respective lumen 1024 and 1124. Removal cartridges 1080 and 1180 may enhance the strength of electrode assemblies 1000 and 1100 and provide straightening and guiding functions.

Figure 12A:
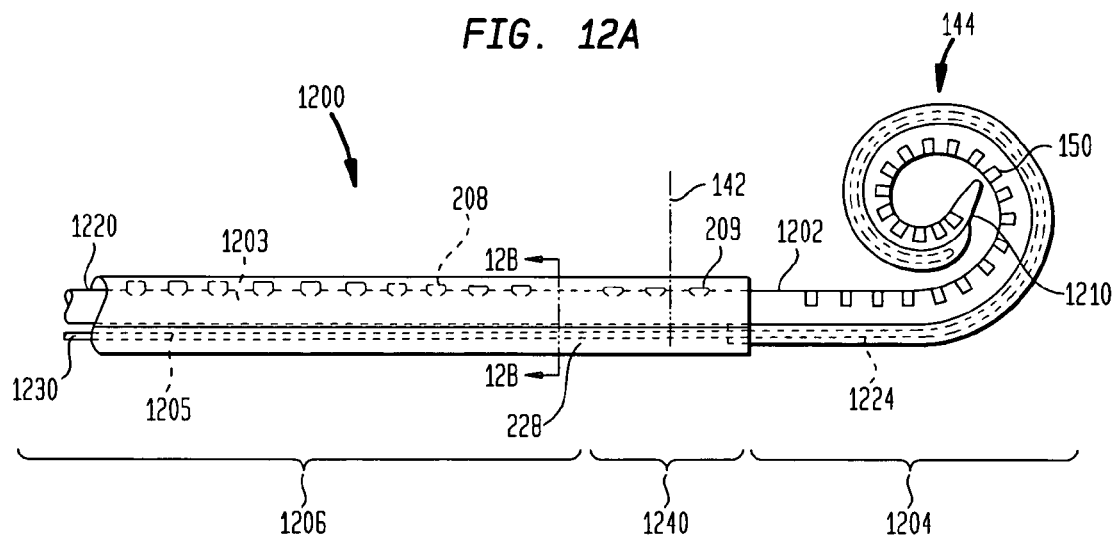
FIG. 12A is a side view of an electrode assembly in accordance with one embodiment of the present invention.
Figure 12B:
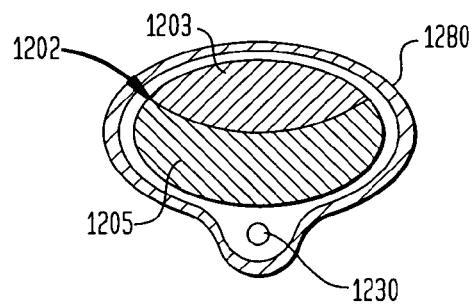
FIG. 12B is a cross-sectional view of the electrode assembly illustrated in FIG. 12A taken along section line 12B-12B.

It should be appreciated that the rails in the above embodiments are optional and that cartridges may be part of the insertion tool. An example of such an embodiment is illustrated in FIGS. 12A and 12B. FIGS. 12A and 12B are side and cross-sectional views, respectively, of one embodiment of electrode assembly 140 illustrated in FIG. 1, referred to herein as electrode assembly 1200. Electrode assembly 1200 has an elongate carrier member 1202 on which an array 144 of electrodes 150 is disposed. Electrode assembly 1200 and, hence, carrier member 1202, has a distal end 1210 at which electrode array 144 is disposed, and a proximal end 1220 which either is connected to, or is proximate to, stimulator unit 134 (not shown in FIGS. 12A and 12B).

This illustrative embodiment of electrode assembly 1200 comprises three contiguous regions: an intra-cochlear carrier region 1204 disposed toward and comprising distal end 1210 of electrode assembly 1200, an extra-cochlear carrier region 1206 disposed toward and comprising proximal end 1220 of electrode assembly 1200, and an incision region 1240 interposed between intra-cochlear carrier region 1204 and extra-cochlear carrier region 1206.

Carrier member 1202 is formed of an upper elongate portion 1203 and a lower elongate portion 1205. A removable cartridge 1280 travels parallel with the longitudinal axis of carrier members 1202. Cartridge 1280 is configured to slidingly receive carrier member 1202 and stylet 1230. As such, carrier member 1202 has a lumen 1224 in intra-cochlear region 1204. Rather, stylet 1230 extends through cartridge 1280 in extra-cochlear region 1206 (not shown) and incision region 1240, and extends through lumen 1205 in intra-cochlear region 1204. In incision region 1240 lower elongate portion 1205 is at least partially absent to provide a non-communicative lumen in incision region 1240, although any of the above or other embodiments of the present invention may be implemented to provide a non-communicative lumen in incision region 1240. Removal cartridges 1280 may be connected to stylet 1230 to enable the surgeon to guide the stylet out of lumen 1224 by removing cartridge 1280.

In the above exemplary embodiments, the carrier member has been described as comprising an upper elongate portion and a lower elongate portion with the lumen extending through the lower elongate portion of one or more contiguous regions of the electrode assemblies. As one of ordinary skill in the art should find apparent, this distinction between upper elongate portion and lower elongate portion is arbitrary and presented for ease of description only. For example, the upper and lower elongate portions of the carrier member may be part of an integrated or unitary carrier member. Furthermore, there is no restriction with regard as to where in the carrier member the lumen is located. For example, the lumen may extend through the lower elongate portion, the upper elongate portion, or some combination thereof.

Although the present invention has been fully described in conjunction with several embodiments thereof with reference to the accompanying drawings, it is to be understood that various changes and modifications may be apparent to those skilled in the art. For example, it should be understood, that any of the above-described embodiments of the present invention may be combined in any way feasible to attain a non-communicative lumen of the present invention. As another example, the foregoing embodiments of the present invention may also have a distal opening in the intra-cochlear lumen or portion of the lumen that extends into the cochlea. This may create an open lumen at the tip. An open lumen would not increase the potential for an transport of organic material across the cochleostomy since the lumen is sealed at incision region 142. Further, the foregoing exemplary embodiments may also be a combination of plugs at any different openings in the lumen to further convert portions of the lumen to non-communicative pathways. As another example, embodiments of the present invention utilize carrier members made of silicone, polymers and/or other biocompatible materials suitable for implantation and which may be configured to attach to electrode assemblies. Also, further applications of stylet insertion devices and carriers are described in the U.S. Pat. No. 6,421,569 and U.S. Patent Published Application Nos. 2004/0236390, 2004/0172118, 2004/0122501, 2004/0030376, 2003/0181967, 2003/0171758, 2003/0093139, 2003/0045921, and 2002/0029074, the entire contents and disclosures of which are hereby incorporated by reference herein. Such changes and modifications are to be understood as included within the scope of the present invention as defined by the appended claims, unless they depart therefrom.

All documents, patents, journal articles and other materials cited in the present application are hereby incorporated by reference.

What is claimed is:

1. An electrode assembly for implantation in a recipient's cochlea via a cochleostomy, comprising:
   an electrode array;
   an elongate carrier member having a lumen extending longitudinally through at least a portion thereof, and having a distal end on which said electrode array is disposed, comprising:
      a distal intra-cochlear region adapted to be implanted in the cochlear and having the lumen extending at least partially therethrough; and
      an incision region, contiguous with the intra-cochlear region, adapted to be partially positioned in the cochlear, wherein the lumen extending therethrough is noncommunicative across the cochleostomy; and
   wherein the lumen is one of either severed, removed, blocked, diverted or interrupted in the region of the carrier which is to be proximate the cochleostomy.

2. The electrode assembly of claim 1, wherein the carrier member further comprises:
   a proximal extra-cochlear region, contiguous with the incision region, adapted to be positioned external the cochleostomy.

3. The electrode assembly of claim 2, wherein the proximal extra-cochlear region is configured such that the lumen extends at least partially through the extra-cochlear region.

4. The electrode assembly of claim 1, wherein at least a portion of the carrier member in the incision region is removed so as to form an aperture in the lumen extending therethrough.

5. The electrode assembly of claim 1, wherein the lumen is configured to receive a stylet.

6. The electrode assembly of claim 1, wherein the portion of the carrier member through which the lumen extends in the incision region is absent.

7. The electrode assembly of claim 1, wherein the portion of the carrier member that is present in the incision region defines an upper surface of the lumen.

8. The electrode assembly of claim 1, wherein the portion of the carrier member that is present in the incision region defines a side surface of the lumen.

9. The electrode assembly of claim 1, wherein the portion of the carrier member that is present in the incision region comprises a plurality of radial slots resulting in a plurality of spaced radial support ribs.

10. The electrode assembly of claim 9, wherein the radial support ribs and the radial slots have substantially the same length.

11. The electrode assembly of claim 9, wherein the radial support ribs are approximately 0.2 to 1.0 mm in length, and wherein the radial slots are approximately 0.2 mm to 1.0 mm in length.

12. The electrode assembly of claim 1, wherein the portion of the carrier member that is present in the incision region comprises a plurality of lateral support ribs collectively supporting a stylet installed in the lumen.

13. The electrode assembly of claim 12, wherein the plurality of lateral support ribs alternate longitudinally along the incision region.

14. The electrode assembly of claim 1, wherein a section of the incision region of the carrier member that forms a circumference of at least a portion of the lumen is removable from the carrier member, wherein when the removable section is removed, the lumen is noncommunicative.

15. The electrode assembly of claim 14, wherein the removable section of the carrier member is formed from a dissolvable/resorbable material.

16. The electrode assembly of claim 15, wherein the dissolvable/resorbable material comprises one or more of the group consisting of polylactic acid (PLA) and polyglycolic acid (PGA).

17. The electrode assembly of claim 14, wherein the removable section of the carrier member is a manually-detachable section of the carrier member.

18. The electrode assembly of claim 1, wherein the carrier member further comprises:
   a raised surface integral with the incision region of the carrier member.

19. The electrode assembly of claim 1, wherein the carrier member is constructed so as to be resistant to bending in the incision region.

20. The electrode assembly of claim 1, wherein the lumen is configured to expand and contract in response to forced insertion and removal, respectively, of a stylet, wherein when the lumen is collapsed the lumen is non-communicative.

21. The electrode assembly of claim 1, wherein the carrier member further comprises a raised surface formed on the incision region wherein a rail is formed at a juncture of the raised surface and the carrier member, and wherein the electrode assembly further comprises:
   a removable cartridge coupled to the stylet and configured to travel on the rail parallel with a longitudinal axis of the carrier member.

22. A prosthetic hearing implant system comprising:
   an electrode assembly for implantation in a recipient's cochlea via a cochleostomy, comprising an electrode array and an elongate carrier member having a lumen extending longitudinally through at least a portion thereof, and having the electrode array disposed therein, the elongate carrier member comprising:
   a distal intra-cochlear region adapted to be implanted in the cochlea, and having the lumen extending at least partially therethrough;
   an incision region, contiguous with the intra-cochlear region, adapted to be partially positioned in the cochlear, wherein the lumen extending therethrough is non-communicative across the cochleostomy; and
   wherein the lumen is one of either severed, removed, blocked, diverted or interrupted in the region of the carrier which is to be proximate the cochleostomy.

23. The system of claim 22, wherein the carrier member further comprises:
   a proximal extra-cochlear region, contiguous with the incision region, adapted to be positioned external the cochleostomy.

24. The system of claim 22, wherein the proximal extra-cochlear region is configured such that the lumen extends at least partially though the extra-cochlear region.

25. The system of claim 22, wherein at least a portion of the carrier member in the incision region is removed so as to form an aperture in the lumen extending therethrough.

26. The system of claim 22, wherein the lumen is one of either severed, removed, blocked, diverted or interrupted in the region of the carrier which is to be proximate the cochleostomy.

27. The system of claim 22, wherein the lumen is configured to receive a stylet.

28. The system of claim 22, wherein the portion of the carrier member through which the lumen extends in the incision region is absent.

29. The system of claim 22, wherein the portion of the carrier member that is present in the incision region defines an upper surface of the lumen.

30. The system of claim 22, wherein the portion of the carrier member that is present in the incision region defines a side surface of the lumen.

31. The system of claim 22, wherein the portion of the carrier member that is present in the incision region comprises a plurality of radial slots resulting in a plurality of spaced radial support ribs.

32. The system of claim 31, wherein the radial support ribs and the radial slots have substantially the same length.

33. The system of claim 23, wherein the portion of the carrier member that is present in the incision region comprises a plurality of lateral support ribs collectively supporting a stylet installed in the lumen.

34. The system of claim 33, wherein the plurality of lateral support ribs alternate longitudinally along the incision region.

35. The system of claim 22, wherein a section of the incision region of the carrier member that forms a circumference of at least a portion of the lumen is removable from the carrier member, wherein when the removable section is removed the lumen becomes noncommunicative.

36. The system of claim 35, wherein the removable section of the carrier member is formed from a dissolvable/resorbable material.

37. The system of claim 36, wherein the dissolvable/resorbable material comprises polylactic acid (PLA).

38. The system of claim 36, wherein the dissolvable/resorbable material comprises polyglycolic acid (PGA).

39. The system of claim 35, wherein the removable section of the carrier member is a manually-detachable section of the carrier member.

40. The system of claim 39, wherein the manually-detachable section of the carrier member is configured to be removable with surgical forceps.

41. The system of claim 22, wherein the lumen is configured to expand and contract in response to forced insertion and removal, respectively, of a stylet, wherein when the lumen is collapsed the lumen is non-communicative.

42. The system of claim 22, wherein the carrier member further comprises a raised surface formed on the incision region wherein a rail is formed at a juncture of the raised surface and the carrier member, and wherein the electrode assembly further comprises:
 a removable cartridge coupled to the stylet and configured to travel on the rail parallel with a longitudinal axis of the carrier member.

43. An electrode assembly for implantation in a recipient's cochlear via a cochleostomy, comprising:
 an elongate stylet;
 an electrode array; and
 an elongate carrier member having a distal end on which said electrode array is disposed, comprising:
  a distal intra-cochlear region adapted to be implanted in the cochlear and having a lumen extending at least partially therethrough; and
  an incision region, contiguous with the intra-cochlear region, adapted to be partially positioned in the cochlear, having a non-communicative extending therethrough;
 an elongate cartridge configured to slidingly receive said stylet and said carrier member; and
 wherein the lumen is one of either severed, removed, blocked, diverted or interrupted in the region of the carrier which is to be proximate the cochleostomy.

44. The electrode assembly of claim 43, wherein the carrier member further comprises:
 a proximal extra-cochlear region, contiguous with the incision region, adapted to be positioned external the cochleostomy.

45. A prosthetic hearing implant system comprising:
 an electrode assembly configured for implantation in a recipient's cochlea via an aperture in the cochlea, comprising an elongate carrier member having a lumen extending longitudinally through at least a portion thereof, and electrodes disposed therein, the elongate carrier member comprising:
  a distal intra-cochlear region adapted to be implanted in the cochlea and having the lumen extending at least partially therethrough;
  an incision region, contiguous with the intra-cochlear region, adapted to be partially positioned in the cochlea, wherein the lumen extending through the incision region is non-communicative across the aperture; and
 wherein the portion of the carrier member present in the incision region comprises a plurality of radial slots resulting in a plurality of spaced radial support ribs.

46. The system of claim 45, wherein the carrier member further comprises:
 a proximal extra-cochlear region, contiguous with the incision region, adapted to be positioned external the aperture.

47. The system of claim 46, wherein the portion of the carrier member present in the incision region comprises a plurality of lateral support ribs collectively supporting a stylet installed in the lumen.

48. The system of claim 45, wherein the lumen is configured to receive a stylet.

49. The system of claim 45, wherein the portion of the carrier member present in the incision region defines an upper surface of the lumen.

50. The system of claim 45, wherein the portion of the carrier member that is present in the incision region defines a side surface of the lumen.

51. The system of claim 45, wherein the radial support ribs and the radial slots have substantially the same length.

52. The system of claim 45, wherein a section of the incision region of the carrier member that forms a circumference of at least a portion of the lumen is removable from the carrier member, wherein when the removable section is removed the lumen becomes noncommunicative.

53. The system of claim 52, wherein the removable section of the carrier member is a manually-detachable section of the carrier member.

54. The system of claim 45, wherein the lumen is configured to expand and contract in response to forced insertion and removal, respectively, of a stylet, wherein when the lumen is collapsed the lumen is non-communicative.

55. The system of claim 45, wherein the carrier member further comprises a raised surface formed on the incision region wherein a rail is formed at a juncture of the raised surface and the carrier member, and wherein the electrode assembly further comprises:
 a removable cartridge coupled to the stylet and configured to travel on the rail parallel with a longitudinal axis of the carrier member.

56. A prosthetic hearing implant system comprising:
an electrode assembly for implantation in a recipient's cochlea via an aperture, comprising an electrode array and an elongate carrier member having a lumen extending longitudinally through at least a portion thereof, and having the electrode array disposed therein, the elongate carrier member comprising:
a distal intra-cochlear region adapted to be implanted in the cochlea, and having the lumen extending at least partially therethrough;
an incision region, contiguous with the intra-cochlear region, adapted to be partially positioned in the cochlea, wherein the lumen extending therethrough is non-communicative across the aperture; and
wherein a section of the incision region of the carrier member that forms a circumference of at least a portion of the lumen is removable from the carrier member, wherein when the removable section is removed the lumen becomes noncommunicative.

57. The system of claim 56, wherein the carrier member further comprises:
a proximal extra-cochlear region, contiguous with the incision region, adapted to be positioned external the cochlea.

58. The system of claim 57, wherein the portion of the carrier member that is present in the incision region comprises a plurality of lateral support ribs collectively supporting a stylet installed in the lumen.

59. The system of claim 56, wherein the lumen is configured to receive a stylet.

60. The system of claim 56, wherein the portion of the carrier member that is present in the incision region defines an upper surface of the lumen.

61. The system of claim 56, wherein the portion of the carrier member that is present in the incision region defines a side surface of the lumen.

62. The system of claim 56, wherein the portion of the carrier member that is present in the incision region comprises a plurality of radial slots resulting in a plurality of spaced radial support ribs.

63. The system of claim 56, wherein the removable section of the carrier member is formed from a dissolvable/resorbable material.

64. The system of claim 56, wherein the removable section of the carrier member is a manually-detachable section of the carrier member.

65. The system of claim 56, wherein the lumen is configured to expand and contract in response to forced insertion and removal, respectively, of a stylet, wherein when the lumen is collapsed the lumen is non-communicative.

* * * * *